(12) United States Patent
Rosenhan et al.

(10) Patent No.: US 11,179,859 B2
(45) Date of Patent: Nov. 23, 2021

(54) SAFETY CUTTING DEVICE (71) Applicant: PenBlade, Inc., Salt Lake City, UT (US)

(72) Inventors: Branden D. Rosenhan, Salt Lake City, UT (US); Benjamin Grover, Granada Hills, CA (US); Timothy R. Nieman, North Salt Lake, UT (US); Andrew S. Hansen, Bountiful, UT (US); Micah Frerck, Salt Lake City, UT (US); Alex Drew, Salt Lake City, UT (US)

(73) Assignee: PenBlade, Inc., Salt Lake City, UT (US)

( * ) Notice: Subject to any disclaimer, the term of this patent is extended or adjusted under 35 U.S.C. 154(b) by 324 days.

(21) Appl. No.: 14/201,658

(22) Filed: Mar. 7, 2014

(65) Prior Publication Data

US 2014/0182140 A1 Jul. 3, 2014

Related U.S. Application Data (63) Continuation of application No. PCT/US2013/073433, filed on Dec. 5, 2013.

(60) Provisional application No. 61/733,433, filed on Dec. 5, 2012.

(51) Int. Cl.
*B26B 5/00* (2006.01)
*A61B 17/3213* (2006.01)
*A61B 17/3211* (2006.01)

(52) U.S. Cl.
CPC .......... *B26B 5/003* (2013.01); *A61B 17/3213* (2013.01); *A61B 2017/32113* (2013.01)

(58) Field of Classification Search
CPC ...... A61B 17/3211; A61B 2017/32113; B26B 1/08; B26B 5/003

USPC .................... 30/62, 162, 151, 335
See application file for complete search history.

(56) References Cited

U.S. PATENT DOCUMENTS

| | | | |
|---|---|---|---|
| 1,456,786 A | | 5/1923 | De Luca |
| 1,701,771 A | * | 2/1929 | di stefano ............. 30/162 |
| 2,112,518 A | | 3/1938 | Caplan |
| 2,198,111 A | * | 4/1940 | Gorbatenko ............. C14B 1/24 |
| | | | 30/162 |
| 2,601,402 A | | 6/1952 | Krause et al. |
| 3,427,113 A | | 2/1969 | Bourbon |

(Continued)

FOREIGN PATENT DOCUMENTS

| | | |
|---|---|---|
| DE | 3003528 | 8/1980 |
| JP | 2008061868 | 3/2008 |
| WO | WO 97/15233 | 5/1997 |

OTHER PUBLICATIONS

International Search Report of PCT/US2013/073433, dated Feb. 18, 2014.

(Continued)

*Primary Examiner* — Ghassem Alie
*Assistant Examiner* — Fernando A Ayala
(74) *Attorney, Agent, or Firm* — Epiphany Law, LLC (57) ABSTRACT

A safety cutting device includes a slidable insert that moves longitudinally within a cavity of a housing. The slidable insert has a cutting blade attached and moves within the housing from a safe position in which the blade is covered to an exposed position for cutting. The safety device has a release button positioned near an anterior end of the housing. A biasing member automatically retracts the blade when the release button is activated.

21 Claims, 4 Drawing Sheets

(56) References Cited

U.S. PATENT DOCUMENTS

| | | | |
|---|---|---|---|
| 3,577,637 A | 5/1971 | Braginetz | |
| 3,657,812 A * | 4/1972 | Lee | B26B 1/08 30/162 |
| 4,337,576 A * | 7/1982 | Drost et al. | 30/162 |
| 4,499,898 A | 2/1985 | Knepshield et al. | |
| 4,604,804 A | 8/1986 | Sparks | |
| 4,683,656 A | 8/1987 | Peyrot et al. | |
| 4,735,202 A | 4/1988 | Williams | |
| 4,769,912 A | 9/1988 | Davis | |
| 5,330,492 A | 7/1994 | Haugen | |
| 5,330,493 A | 7/1994 | Haining | |
| 5,391,177 A | 2/1995 | Schwartz | |
| 5,503,262 A | 4/1996 | Baudat et al. | |
| 5,569,282 A | 10/1996 | Werner | |
| 5,571,127 A | 11/1996 | DeCampli | |
| 5,571,128 A | 11/1996 | Shapiro | |
| 5,599,351 A | 2/1997 | Haber et al. | |
| 5,662,669 A | 9/1997 | Abidin et al. | |
| 5,665,099 A | 9/1997 | Pilo et al. | |
| 5,768,787 A | 6/1998 | Ireland | |
| 5,779,724 A * | 7/1998 | Werner | 606/167 |
| 5,924,203 A * | 7/1999 | Huang | 30/142 |
| 6,022,364 A | 2/2000 | Flumene et al. | |
| 6,032,553 A | 3/2000 | Puig et al. | |
| 6,254,621 B1 * | 7/2001 | Shackelford et al. | 606/167 |
| 6,503,262 B1 | 1/2003 | Edens | |
| 6,516,520 B1 | 2/2003 | Liao | |
| 6,540,763 B2 | 4/2003 | Teo et al. | |
| 6,589,258 B2 | 7/2003 | Pilo et al. | |
| 6,623,499 B1 | 9/2003 | Andreini et al. | |
| 6,645,216 B2 * | 11/2003 | Masury et al. | 606/167 |
| 6,757,977 B2 | 7/2004 | Dambal et al. | |
| 6,874,188 B2 * | 4/2005 | Johnson | B26B 5/0017/158 |
| 6,949,109 B2 * | 9/2005 | Iske et al. | 606/167 |
| 7,087,067 B2 | 8/2006 | Kehr et al. | |
| 7,101,382 B2 | 9/2006 | George et al. | |
| 7,153,317 B2 | 12/2006 | Kanodia et al. | |
| 7,201,760 B2 | 4/2007 | Masury et al. | |
| 7,316,070 B2 * | 1/2008 | Green | 30/162 |
| 7,765,701 B2 | 8/2010 | Okada | |
| 7,900,362 B2 | 3/2011 | Djordjevic et al. | |
| 8,465,512 B2 | 6/2013 | Rosenhan | |
| 2004/0098004 A1 * | 5/2004 | George | A61B 17/3211 606/167 |
| 2004/0111106 A1 * | 6/2004 | Iske | A61B 17/3211 606/167 |
| 2004/0181247 A1 * | 9/2004 | Kehr | A61B 17/3213 606/167 |
| 2004/0244206 A1 | 12/2004 | Perlmutter et al. | |
| 2005/0021064 A1 | 1/2005 | Lee | |
| 2005/0033336 A1 | 2/2005 | Yang | |
| 2005/0065541 A1 | 3/2005 | Abidin et al. | |
| 2005/0101978 A1 * | 5/2005 | Ziemer | A61B 90/94 606/167 |
| 2006/0241664 A1 * | 10/2006 | Lam | 606/167 |
| 2006/0241665 A1 | 10/2006 | Bosley et al. | |
| 2007/0078472 A1 | 4/2007 | Singh | |
| 2007/0088374 A1 * | 4/2007 | Masury et al. | 606/167 |
| 2009/0157110 A1 | 6/2009 | Muto et al. | |
| 2011/0041345 A1 * | 2/2011 | Austin | 30/162 |
| 2011/0283840 A1 | 11/2011 | Brucart-Puig | |
| 2012/0073143 A1 | 3/2012 | Honda | |
| 2012/0259352 A1 | 10/2012 | Rosenhan | |
| 2013/0245655 A1 * | 9/2013 | Mahurkar | 606/167 |
| 2013/0245656 A1 | 9/2013 | Austria | |
| 2013/0305542 A1 | 11/2013 | McChesney | |
| 2017/0167830 A1 | 6/2017 | Ota | |

OTHER PUBLICATIONS

Extended European Search Report of EP 11850250.9, dated Oct. 16, 2014.
Search Report for Chinese Patent Application No. 2018102803756, "Safety Cutting Device" dated May 20, 2020.
U.S. Appl. No. 14/201,658 is a continuation of U.S. Appl. No. 14/201,658, and both claim priority to PCT/US2013/073433.

* cited by examiner

SAFETY CUTTING DEVICE

CROSS REFERENCE TO RELATED APPLICATIONS

This application is a continuation of International Application No. PCT/US2013/073433, filed on Dec. 5, 2013, which claims the benefit of and priority to U.S. Provisional Application No. 61/733,433, filed on Dec. 5, 2012, the entirety of which is incorporated herein by reference.

BACKGROUND

Field of Use

The present invention relates to cutting devices such as safety scalpels and safety cutting devices.

Related Technology

Surgical scalpels are used by medical personnel in connection with surgical procedures ranging from simple outpatient procedures to extraordinarily complex procedures carried out under general anesthesia. When working with such a sharp instrument, there is always a danger to medical personnel of inadvertent puncture of the skin. Aside from the injury itself, the more important concern for the punctured individual relates to the potential spread of disease from a non-sterile instrument.

The use of surgical scalpels having a retractable blade has been suggested as a means for reducing the number of such puncture wounds. Indeed, a number of patents have been issued which are directed toward surgical scalpels having retractable blades. These include, for example, U.S. Pat. Nos. 5,503,262; 5,571,128; 5,569,282; 6,589,258; 6,645,216; and 6,949,109.

A tremendous effort has been made to make cutting devices that will improve safety in health care and industry. Government agencies such as OSHA have mandated the use of safer cutting devices. The industry including large medical device manufacturers and small entrepreneurial companies and individuals have attempted to produce devices that improve safety. However, studies have shown that the industry thus far has failed. For example, an industry published journal "OR Manager" published the following statement: "The products just aren't there. Unfortunately, it's hard to be compliant when we don't have good technology." See OR Manager Vol. 21, No. 12, December 2005, p. 3. Indeed, data shows that current safety scalpels are actually not safer than traditional reusable scalpels. see Vose, J. et al., "Reducing Scalpel Injuries in the OR," AORN Journal, Vol. 90, No. 6 (December 2009), p. 869. Thus, there exists a long felt but unmet need for improved safety scalpels that can reduce sharps injuries.

DETAILED DESCRIPTION

The present invention relates to safety cutting devices. The devices of the present invention have one or more improved mechanisms for activating and retracting the blade to make the cutting device safe when not in use. The activation and retraction features are intuitive and in many embodiments allow a clinician to operate the features using a single hand without looking. In addition, the safety mechanisms in some embodiments can be implemented with a minimal number of parts, thereby making the devices easy and economical to manufacture and assemble. For example, some embodiments can be manufactured with as few as 5 parts (e.g., a blade, a spring, and 3 injection molded pieces).

FIGS. 1A-1C and 2 illustrate an example safety cutting device 10 according to one embodiment of the invention. Device 10 includes a cutting blade 12 connected to a slidable insert 14. Slidable insert 14 is configured to move within an elongate housing 16. Elongate housing 16 includes a cavity 18 (FIG. 4) that extends between an anterior opening 20 at an anterior end 22 of housing 16. A posterior opening 24 is formed at an opposite end of housing 16 in longitudinal direction.

Housing 16 forms a sheath 30 that is configured to house the blade and protect it from cutting a person. Sheath 30 defines the anterior opening 20 through which cutting blade 12 can be extended to expose cutting blade 12 and allow device 10 to be used as a cutting instrument.

The slidable insert 14 and the housing 16 are configured with any number of walls, grooves, ridges, protrusions and/or indentations to allow slidable insert 14 to move within housing 16 in a slidable manner between a safe position in which cutting blade 12 is within sheath 30 and an exposed position in which cutting blade 12 is extended through anterior opening 20. The direction of movement of slidable insert 14 may be in the longitudinal direction 28 (identified by arrow 28 in FIG. 2), which is preferably along the longitudinal axis of elongate housing 16 (either forward or backward).

Unless otherwise specified, the anterior opening is the furthest anterior point on the housing in the longitudinal direction from which the blade emerges during activation.

Unless otherwise specified, the posterior opening is the location on the housing where a posterior activation mechanism (e.g., a back button) emerges from the housing. The posterior opening may be open in the longitudinal direction or partially or completely opened toward a side, bottom, or top of the housing. Where the posterior activation mechanism includes a longitudinal post the opening is preferably in the longitudinal direction.

Unless otherwise specified, the longitudinal direction is the plane in which the slider moves when going from the safe position to the exposed position or the exposed position to the safe position.

Figure 1A:
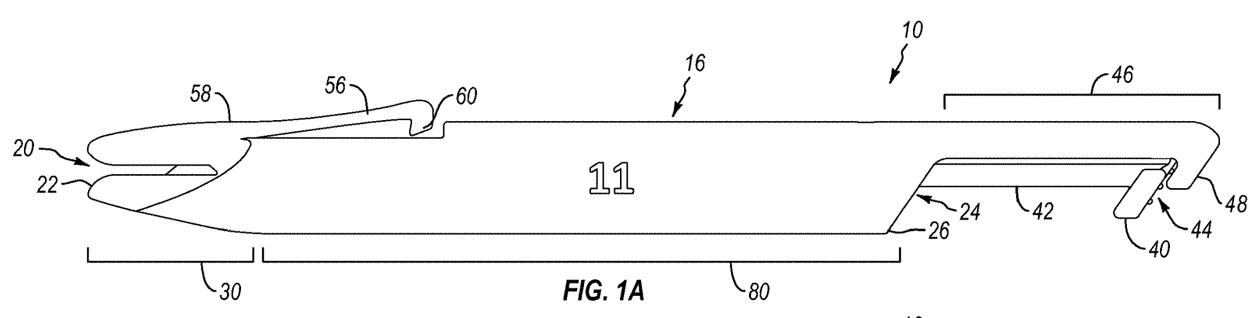
FIG. 1A is an elevational view of a safety cutting device with the blade in a covered position according to one embodiment of the invention.
Figure 1B:
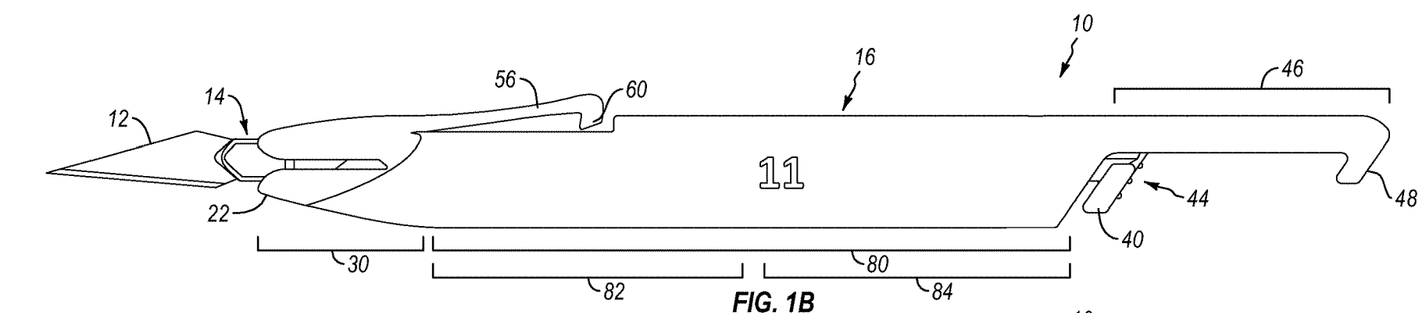
FIG. 1B is an elevational view of the cutting device of FIG. 1A with the blade in an exposed position.
Figure 1C:
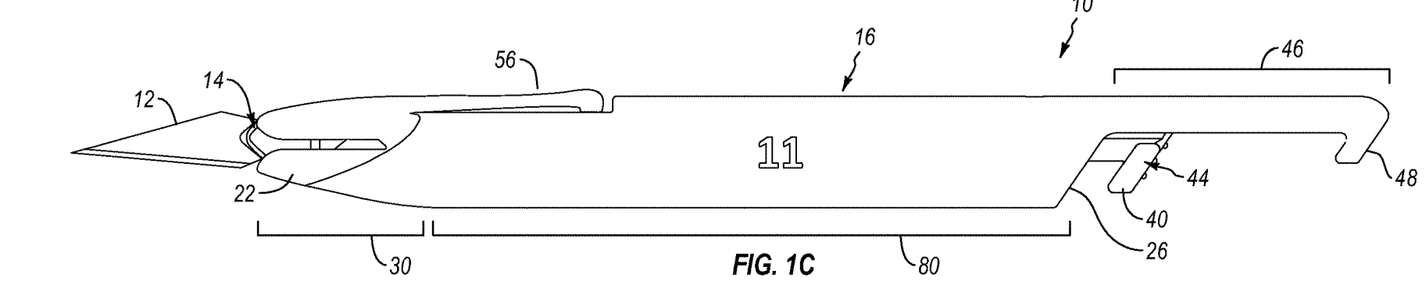
FIG. 1C is an elevational view of the cutting device of FIG. 1A with blade in an exposed position and a release button actuated.

FIGS. 1A and 1B show blade 12 in the safe position and the exposed position, respectively. Additional details regarding movement of slidable insert 14 are described below with regard to FIGS. 3A-3C.

Figure 2:
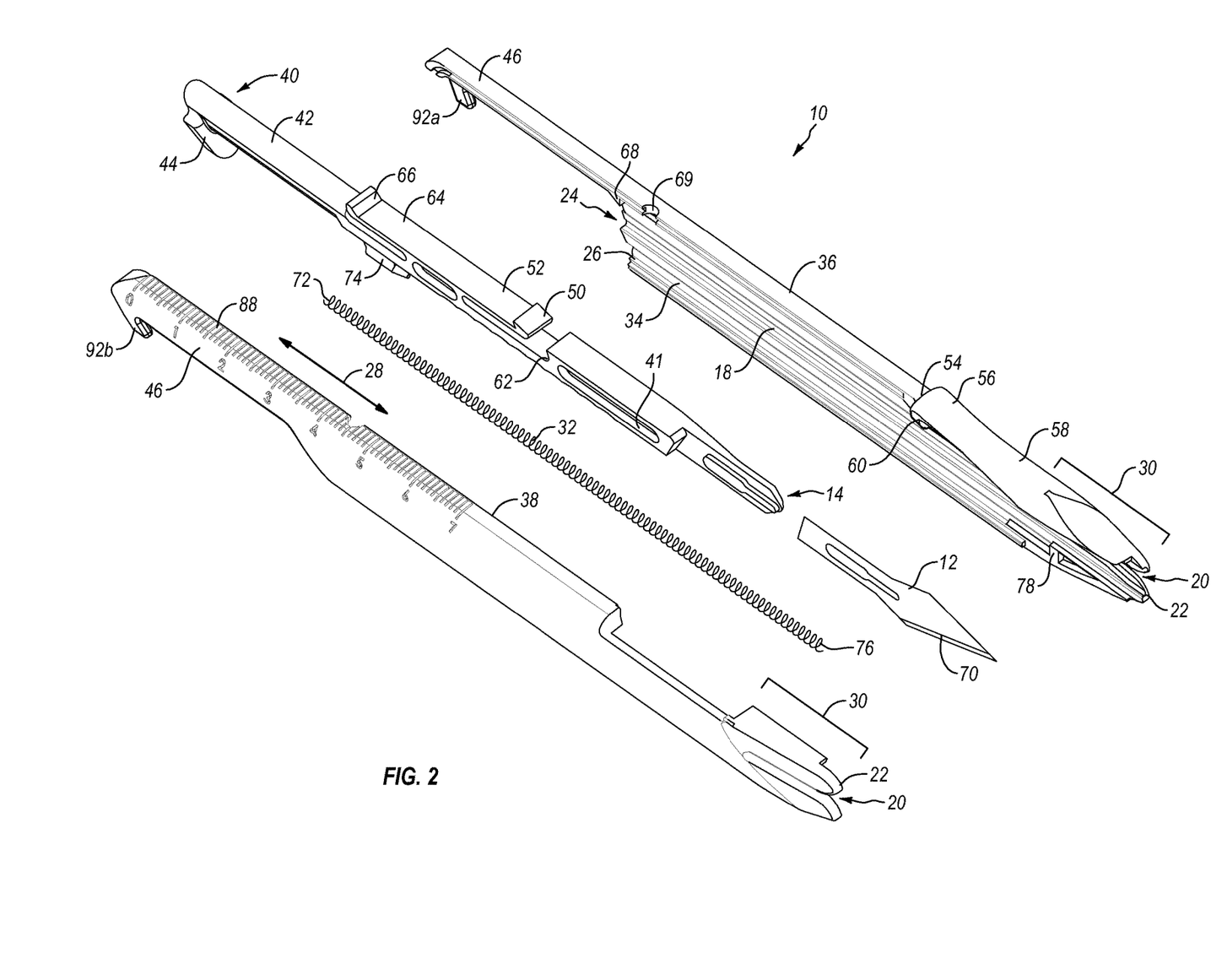
FIG. 2 illustrates an exploded view of the cutting device of FIG. 1A.

As shown in FIG. 2, housing 16 may be formed from a plurality of individual sections, such as left section 36 and right section 38. Any number of sections can be formed and can be attached in any known way to make a cavity 18 suitable for slidable insert 14 to move inside housing 16. Housing sections 36 and 38 may be joined by snap connects, ultrasonic welding, adhesive, or the like.

The junction of left section 36 and right section 38 may create a track 34, half of which is visible in left section 36 of FIG. 2. Track 34 is configured to receive a biasing member 32. In some embodiment biasing member 32 may be a coil spring that undergoes compression or extension. Slidable insert may have a spring connector 74 (e.g., a protrusion) for engaging biasing member 32. In other embodiments, the biasing member may be positioned around or in slidable insert 14 and may be something other than a coil spring.

In some embodiments, with slidable insert 14 in the exposed position, housing 16 may engage slidable insert 14 on multiple sides to provide stability for blade 12. For example, slidable insert may contact sheath 30 on at least 3, preferably 4 sides so as to stabilize blade 12 relative to housing 16. The engagement can be achieved by tapering the inside surfaces of sheath 30 of housing 16. In some embodiments anterior end 22 of housing 16 may taper on an inside surface to decrease the tolerances between slidable insert 14 and housing 16 with the slidable insert in the exposed position. Decreasing the tolerances at anterior end 22 reduces wiggle or play in the blade relative to the housing. In some embodiments, the tolerances may be less than or equal to 0.010, 0.007, or 0.005 inch. The tolerances can be selected in a vertical or a horizontal direction (where the vertical direction is parallel to the plane of the blade).

In some embodiments sheath 30 may be tapered on an outside surface to reduce the width of housing 16 near anterior end 22. Tapering on the outside near anterior end 22 provides greater visual access to the tissue or object being cut by the blade.

Blade 12 may be connected to slidable insert by heat staking a raised portion 41 of slidable insert to blade 12. Alternatively, slidable insert 14 may be injection formed around blade 12.

Device 10 includes a posterior activation mechanism 40 that includes a longitudinal post 42 and a rearward facing engagement surface 44. A protective cover 46 extends from posterior opening 24 to a posterior end 48 of protective cover 46, which is also a posterior end 48 of housing 16 and device 10. Protective cover 46 can also include lateral extensions 92a and 92b.

Housing 16 and slidable insert 14 can include components sufficient to form one or more latches or locking mechanism to hold slidable insert 14 in the extended position (i.e., against the biasing member). In some embodiments, moving slidable insert 14 from the safe position to the exposed position automatically actuates the latching mechanism. In some embodiments the components of a latch include an anterior protrusion 50 on a deflectable member 52 of slidable insert 14. Protrusion 50 is configured to engage a latch surface 54 of housing 16. Device 10 may also include components for releasing a latch or lock mechanism. For example, device 10 may include a release button 56 extending from housing 16 through flange 58. Release button 56 may include a protrusion 60 that engages anterior protrusion 50 to cause deflection of member 52 of slidable insert 14 to release the latch.

Device 10 may include a second locking mechanism formed from housing 16 and slidable insert 14. Second locking mechanism may be formed between protrusion 60 of release button 56 that engages a lock surface 62 of slidable insert 14.

Slidable insert 14 may also include components that facilitate simple assembly. In the embodiment illustrated in FIG. 2, slidable insert 14 include a posterior deflectable member 64 having a protrusion 66. An assembly protrusion 68 on housing 16 is configured to deflect member 64 on assembly and engage protrusion 68 to prevent slidable insert 14 from being ejected from cavity 18 after assembly.

Figure 3A:
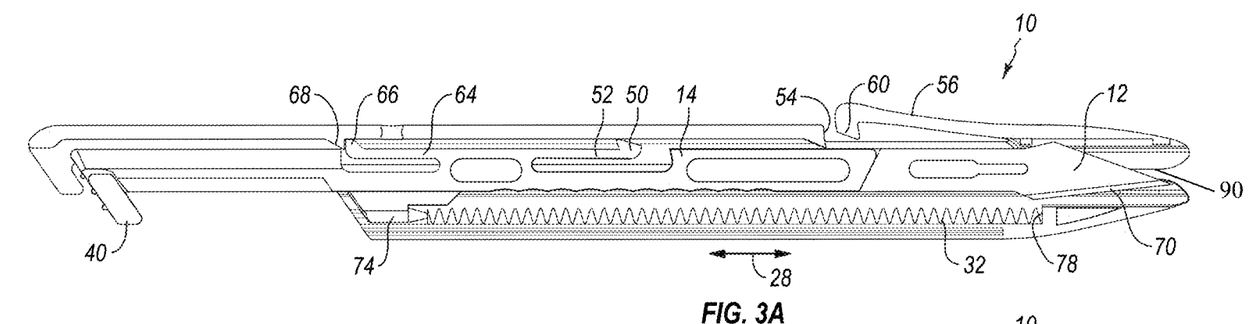
FIG. 3A is a partial cutaway view of the cutting device of FIG. 1A in a covered position and showing the engagement of a slidable insert support and a portion of a housing.
Figure 3B:
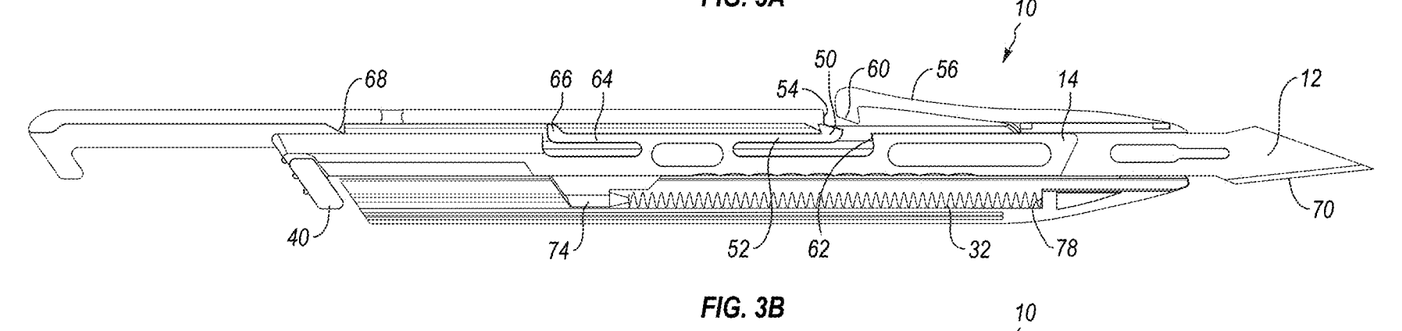
FIG. 3B illustrates the partial cutaway view of FIG. 3A with the cutting device in an exposed position.
Figure 3C:
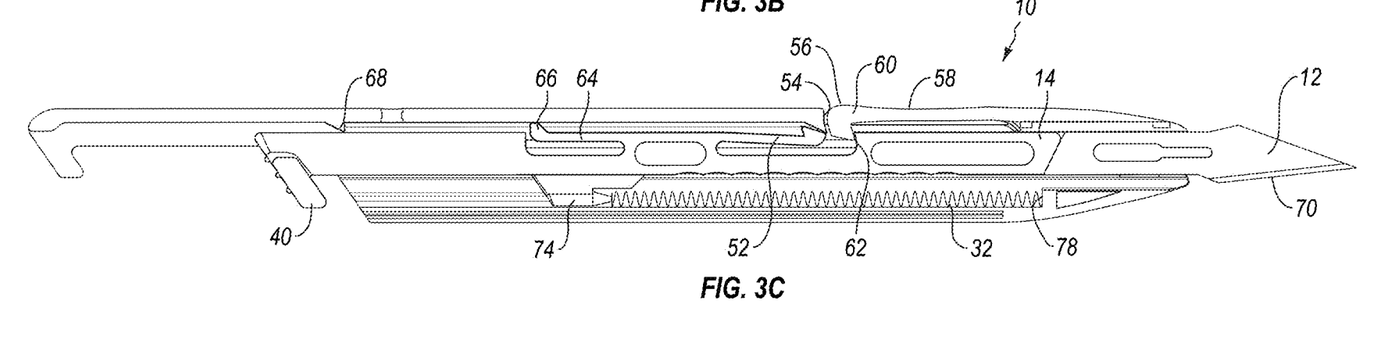
FIG. 3C illustrates the partial cutaway view of FIG. 3A with the blade in an exposed position and the release button in an actuated position.

FIGS. 3A-3C illustrate the scalpel with a portion of the housing removed to reveal the mechanisms of activation, latch release, and slidable insert in a safe position, latched position, and locked position, respectively. In FIG. 3A, device 10 has slidable insert 14 in a safe position. Blade 12 is within sheath 30, which provides protection against a person being cut by cutting edge 70 of blade 12.

Biasing member 32, which may be a coil spring in some embodiments, sits in track 34 and biases slidable insert 14 in the safe position. Biasing member 32 has a back end 72 that engages connector 74 of slidable insert 14 (e.g., a longitudinal pin). A front end 76 of biasing member 32 engages end wall 78 of track 34. Track 34 may be formed from the assembly of left and right sections of housing 16, each of which includes a portion of the track. Although forming the track from two pieces is not required. Slidable insert 14 is moveable in the longitudinal direction 28 toward the anterior end 22. FIG. 3B shows device 10 with slidable insert 14 in the exposed position. As shown by the difference between FIGS. 3A and 3B, a forward movement of slidable insert 14 in the longitudinal direction causes biasing member 32 to compress, thereby increasing or maintaining the biasing force (in this case compression) as the slidable insert moves into the exposed position. Thus, absent a locking mechanism slidable insert is pushed back towards the safe position. The spring force can be selected to ensure the friction caused by the selected tolerances does not cause the slidable insert to stick when the latch mechanism is released.

In some embodiments, housing 16 and slidable insert 14 automatically form a lock when slidable insert 14 is moved into the exposed position. As slidable insert 14 is moved forward, anterior protrusion 50 positioned on or near the end of deflectable member 52 engages protrusion 54 of housing just as blade 12 is nearing the extended position. Protrusion 50 on slidable insert 14 and protrusion 54 can have anterior and posterior ramps, respectively such that the forward movement of slidable insert 14 causes the protrusions to engage in a sliding manner. This sliding movement of the ramps forces deflectable member 52 to flex and protrusion 50 to move downward, thereby passing over protrusion 54. However, once protrusions 50 and 54 pass one another (via the movement of slidable insert 14), deflectable member 52 snaps back. The anterior surface of protrusion 54 and the posterior surface of protrusion 50 are relatively parallel to one another, which causes them to lock when biasing member 32 pushes slidable insert 14 backward. This mechanism often produces a "click" sound, which provides an audible notification to the user that the blade is in the exposed position. This mechanism is also referred to herein as a "click latch mechanism." Although not required, in some cases an audible or tactile feedback of activation may be very important for a clinician to be assured that the device is in the proper configuration before attempting to cut, particularly since the slidable insert is biased to move out of the exposed position.

As shown in FIG. 3C, device 10 may include a release button 56 to release the latch mechanism locking slidable insert 14 in the exposed position. Release button 56 includes a protrusion 60 that when moved downward engages protrusion 50 and forces deflectable member 52 downward a sufficient distance to release the latch between protrusion 50 on slidable insert 14 and protrusion 54 on housing 16.

In some embodiments, protrusion 60 includes an anterior surface 80 that can engage a locking surface 62 on slidable insert 14 when release button 56 is activated. Locking surface 62 may be a substantially perpendicular wall of slidable insert 14 (perpendicular to the longitudinal direction). FIG. 3C shows release button with deflectable member 52 deflected downward and protrusion 60 contacting surface 62 so as to lock slidable insert 14 in the exposed position even though the latch mechanism has been deactivated. This dual locking function allows a user to automatically activate the latch mechanism and change hand position without the blade retracting. Actuating release button 56 releases the lock mechanism involving surface 62 and then releasing release button 56 disengages protrusion 60 from surface 62, thereby releasing the lock on slidable insert 14 and allowing biasing member 32 to automatically return slidable insert 14 to the safe position, which returns device 10 to the position illustrated in FIG. 3A.

Release button 56 may be biased to the non-actuated position (e.g., the position shown in FIGS. 3A and 3B. Any biasing means may be used. In the embodiment shown in FIG. 3A, biasing may be achieved by creating button 56 with a flange 58. Flange 58 may be an integral and/or continuous extension of the housing material. The thickness and/or length of flange 58 may be selected to enable deflection of the button by a user. Those skilled in the art will recognize that the thickness and length of the flange will depend on the type of material being used and the desired rigidity of the release button. In some embodiments, the thickness is less than 4, 2, or 1 mm and/or greater than 0.5, 1, or 1.5 mm or within a range thereof. The length of flange 58 may be greater than or equal to 5, 10, or 15 mm and/or less than 35, 30, or 25, and/or within a range of the foregoing. By forming the button as a single piece with the housing, the number of parts that need to be produced and assembled can be minimized.

Housing 16 is configured to provide a handle 80 (FIG. 1) for the user to hold device 10. Handle 80 allows a user to grip the device for actuating a posterior activation mechanism (e.g., a back button) 40 and actuating a safety release mechanism 56, and/or manipulating device 10 during a cutting procedure.

The configuration of handle 80 and the position of the release and activation mechanisms (e.g., back button 40 and/or release button 56) relative to handle 80 is important in some embodiments to making device 10 intuitive to activate and/or make safe (i.e., retract blade 12). Placing posterior activation mechanism 40 in a position posterior to handle 80 allows activation similar to a pen. Or in other words, when gripping handle 80 a user's thumb is in a position to actuate the activation mechanism 40; after actuating mechanism 40 the user transitions the anterior end 22 to a position between the index, middle, and thumb fingers. While this transition requires significant manipulation of the device, the muscle memory for performing the manipulation is well-known to essentially every clinician due to the ubiquity of click pens. Moreover, Applicant has found that manipulating the device prior to making a cut versus after a cut is more acceptable to clinicians because attention to the patient is more urgent immediately after making an incision. Placing the release mechanism on an anterior portion of housing 16 allows the clinician to release the mechanism with minimal manipulation. Applicant has surprisingly found that placement of the release mechanism in the anterior portion of the device does not result in accidental deployment as one of skill in the art would expect.

Handle 80 may be made to have dimensions suitable for a person to grasp the handle and actuate the buttons. Handle 80 may be elongate with a length greater than or equal to 15, 20, 25, 30, 35, 45, or 55 mm long and/or less than or equal to 120, 100, 80, or 60 mm and/or within a range of any of the foregoing endpoints. In some embodiments, the handle 80 of housing 16 can constitute the majority of the outer surface of housing 16. Handle 80 may include an front portion 82 (FIG. 1B) and a back portion 84 (FIG. 1B). For purposes of this invention, unless otherwise specified, the front portion 82 is the front half of handle 80 as measured in the longitudinal direction and the back portion 84 is the back half of handle 80. The handle portion 80 is the portion of the housing that is useful as a gripping surface during use. In some embodiments, front portion 82 may have a length in the longitudinal direction that is greater than or equal to 10, 15, 20, 25, 30, 35, or 40 mm and/or less than or equal to 80, 60, 50, 40, or 30 mm, and/or within a range of the foregoing. Front portion 82 and sheath 30 form the anterior portion of housing 16.

Release button 56 may be positioned on the anterior portion of housing 16 (i.e., sheath 30 and/or front portion 82). For example, release button 56 may be positioned near anterior opening 20. Release button 56 may be positioned less than or equal to 40, 35, 30, 25, 20, 15, or 10 mm and/or greater than 5, 10, 15, or 20 mm from anterior opening 20 in sheath 30 and/or within a range of the foregoing. Release button 56 may be positioned less than or equal to 50%, 45%, 40%, 35%, 30%, 25%, or 20% of the longitudinal distance from the anterior opening 20 to the posterior opening 24.

Positioning release button 56 on the anterior portion of housing 16 and/or near anterior opening 20 makes the release button easy and intuitive to actuate. When a user's fingers are positioned for manipulating device 10 to perform a cutting procedure, the index finger and/or thumb will be in contact with the anterior portion. Because the fingers are already located in the anterior portion of housing 16, a user can easily feel release button 56 with little to no hand movement. This tactile feedback allows a physician to actuate release button 56 without repositioning the hand on handle 80.

Handle 80 may also serve as a grip for activating posterior activation mechanism 40. In this case, the fingers such as the index finger may be positioned on the posterior portion of housing 16 (i.e., the thumb is extended rearward). The thumb may be placed on the rearward facing engagement surface 44 and drawn toward the back portion 84, thereby actuating mechanism 40.

Handle 80 may have any type of configuration suitable for providing a place for a person to hold device 10 while actuating posterior mechanism 40 or anterior release button 56. Handle 80 may have a cross section that is contoured, circular, rectangular, or the like. The cross section of handle 80 may be elongate from top to bottom as compared to the width (e.g., oval or trapazoidal). In some embodiments, handle 80 may have an average thickness (i.e., distance in a direction transverse to blade 12) that is greater than or equal to 4, 5, 6, 8, or 10 mm and/or less than or equal to 14, 12, 10, 8, or 6 mm or within a range of the forgoing endpoints. These thicknesses provide adequate space for a relatively large blade while still providing comfort and usability for an adult or clinician.

Handle 80 may also include gripping features to improve the feel and/or texture of handle 80. For example, handle 80 may include texturizing that gives the user a more tactile feel about where their hands are positioned on handle 80. Handle 80 may also include a ruler 88 or other indicia.

The sheath 30 and/or anterior opening 20 of housing 16 is configured to accommodate the a relatively large blade. For example, blade 12 is a standard sized 11 blade, which has a blade height of 6.5 mm. In some embodiments, the housing 16 may accommodate a blade height of at least 5, 6.5, or 7.5. The blade may a 10 blade, 11 blade, 15 blade, or other standard sized blade.

Sheath 30 can include a slot 90 that extend inward from anterior end 20. Slot 90 forms a suture cutting groove that allows a suture to be passed therethrough when blade 12 is retracted (i.e., covered by sheath 30). Additional details regarding suture cutting grooves that can be implemented in safety device 10 are disclosed in U.S. application Ser. No. 13/080,367, filed Apr. 5, 2011, which is hereby incorporated herein by reference.

In some embodiments (were a relatively constant biasing force is needed or required), biasing member may be relatively long, preferably longer than the distance slidable insert 14 travels between the safe position and exposed position. For example, the length of biasing member 32 may be at least 1.25, 1.5, 2, 2.5, or 3 times longer than the longitudinal travel of slidable insert 14 between the safe position and the open position. In some embodiments the biasing member 32 may be at least 15, 20, 25, 30, 35, 45, or 55 mm long and/or less than 120, 100, 80, or 60 mm and/or within a range of any of the foregoing endpoints. In some embodiments, biasing member extends at least 70%, 80%, or 90% of the distance between anterior opening 20 and posterior opening 24 of cavity 18 or a handle portion of housing 16. Relatively long biasing members can be advantageous for maintaining a similar bias at different lengths of compression or extension.

The force of biasing member is selected to be greater than the friction encountered when moving the slider from the exposed position to the safe position. Biasing member 32 may be something other than a coil spring. For example, an elastic material may be used. In addition, the biasing member may be under tension rather than compression. For example the housing and slidable insert may each have a connector attached to the biasing member. In this case, the slidable insert connector may be anterior to the housing connector such that forward movement of the sliding connector causes the biasing member to undergo tension rather than compression.

Figure 4:
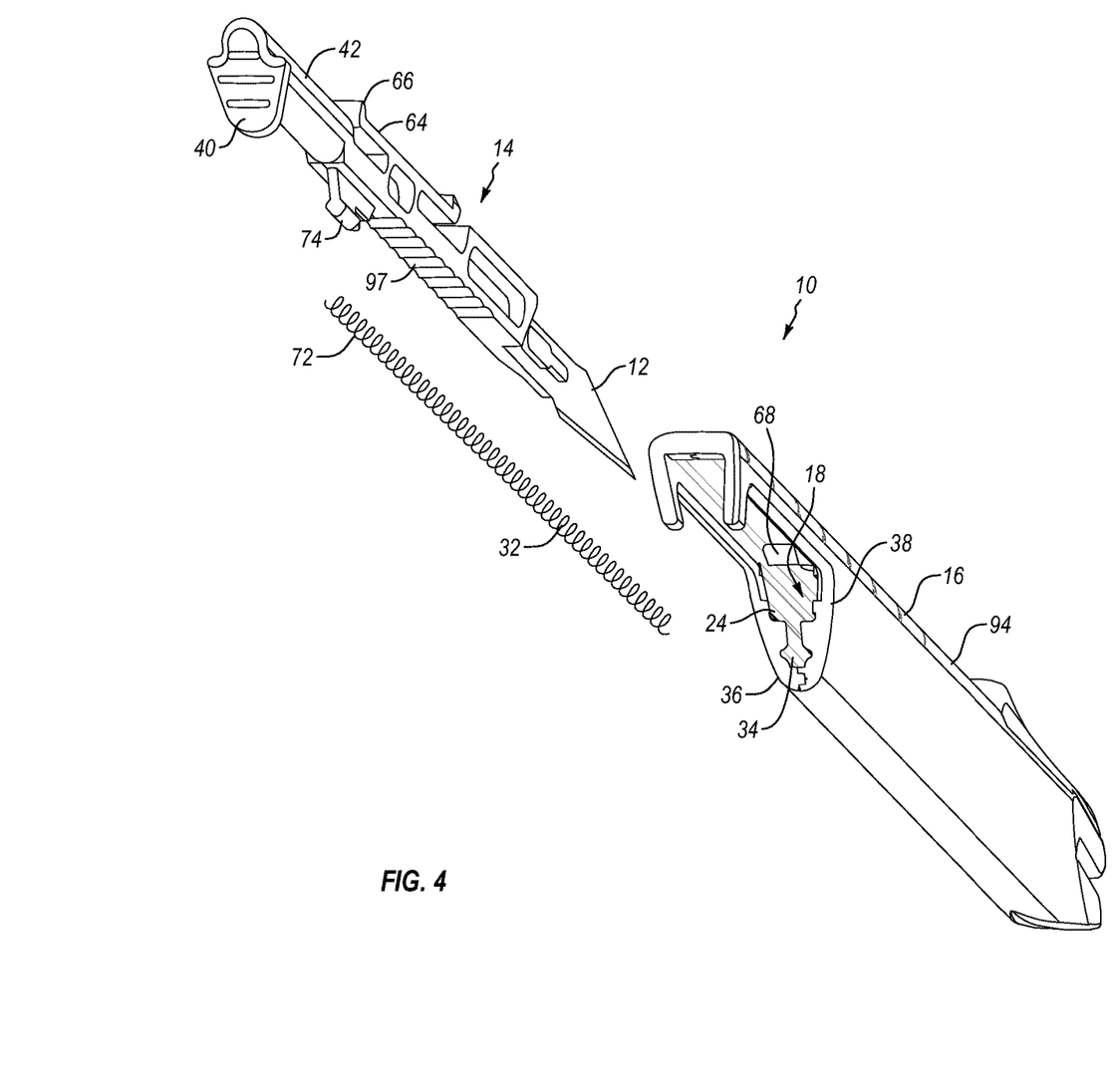
FIG. 4 shows a partial exploded view of the cutting device of FIG. 1A showing the slidable insert, spring, and assembled housing.

FIG. 4 illustrates device 10 partially assembled and showing a perspective view of posterior opening 24 leading to cavity 18. Device 10 may be easily and economically assembled by inserting slidable insert 14 into cavity 18, which is formed between left and right sections 36 and 38 of housing 16. Prior to inserting slidable insert 14 into cavity 18, biasing member 32 is positioned in track 34. As slidable insert 14 is inserted into cavity 18, connector 74 on slidable insert 14 engages back end 72 of biasing member 32.

Biasing member 32 is compressed in track 34 until assembly protrusion 66 engages protrusion 68 on housing 16. Assembly protrusion 66 and protrusion 68 on housing 16 may have a forward facing ramp and reward facing ramp, respectively, such that engagement of the protrusions causes assembly deflection member 64 to be deflected downward as assembly protrusion 66 passes over protrusion 68 on housing 16. Assembly protrusion 66 and protrusion 68 on housing 16 have substantially parallel forward facing and rear facing surfaces, respectively. Once assembly protrusion 66 passes protrusion 68, reward movement of assembly protrusion 66 is inhibited by the substantially parallel surface.

Some embodiments include methods for assembling device 10. The method can include providing a slidable insert with an assembly protrusion. The method can include first assembling the housing to form a cavity for the slidable insert and then inserting the slidable insert into the cavity.

FIG. 4 shows a bottom portion of slidable insert 14 having ribs 97. Ribs 97 can reduce friction and prevent slidable member 14 from sticking when it retracts.

The cutting instruments described herein may be used in methods for performing a cutting procedure. In some embodiments, the cutting procedure may be a procedure to cut live tissue. In other embodiments the cutting procedure may be a non-medical substrate. For example, the cutting devices described herein may be configured and used for non-medical purposes such as cutting crafts, rope, string, cardboard, paper, and the like.

In some embodiments, housing 16 may include a pen clip that allows device 10 to be clipped to a shirt pocket. Typically the clip opens toward an anterior end such that the blade is facing downward when clipped to a pocket (e.g., a traditional shirt pocket).

The color and/or translucency of device 10 may assist some users in using device 10. In some embodiments, sheath 30 and/or handle 80, and/or cover 46, may be made from a translucent material such as carbonate to allow the user to see the internal components of safety device 10. Sheath 30 may be translucent to reveal blade 12 when retracted.

Posterior Activation Mechanism with Anterior Release Mechanism

Some embodiments of the invention are directed to a cutting device having a posterior activation mechanism and an anterior release mechanism. The posterior activation mechanism requires activation by a motion from the posterior towards the anterior. (e.g., a back button that activates the blade in a manner similar to a ball point pen) and has a release button in the anterior portion of the housing for retracting the blade. This configuration is advantageous because the activation of the blade is intuitive and simple since all clinicians are familiar with the mechanism for activating a ball point pen. In addition, the placement of the release button in the anterior portion of the housing allows the device to be made safe without requiring the clinician to look at the device or repositioning the hand after cutting, which allows a clinician to focus on the incision made rather than focus on the safety features of the device.

In some embodiments, the safety cutting device may include an elongate housing having a lengthwise cavity that extends between an anterior opening and a posterior opening. The cavity is configured to receive a slidable insert and allow movement of the slidable insert in a longitudinal direction. A cutting blade is coupled to the slidable insert. The housing forms a sheath configured to cover the cutting blade. The sheath provides the anterior opening through which the blade can be extended. The slidable insert is moveable within the housing between a safe position in which the blade is covered by the sheath and an exposed position in which the blade is extended through the anterior opening and exposed for cutting. A biasing member is operably coupled to the slidable insert and biases the slidable insert to the safe position.

The safety cutting device also includes a latch mechanism operable to lock the slidable insert in the exposed position.

A back button is formed in or coupled to the slidable insert and extends from the posterior opening in the housing, the back button has a rearward facing engagement surface that upon actuation moves the slidable insert longitudinally from the safe position to the exposed position. The housing forms a handle and an front portion of the handle provides a grip for manipulating the cutting device with fingers while performing a cutting procedure. A release button is positioned on the anterior portion of the housing. The release button is configured to unlock the latch mechanism upon actuation and allow the biasing member to return the slidable insert to the safe position.

The release button is positioned near the anterior opening. The release button may be positioned less or equal to 40, 35, 30, 25, 20, 15, or 10 mm and/or greater than 5, 10, 15, or 20 mm from the anterior opening of the sheath and/or within a range of the foregoing. The release button may also be positioned less than or equal to 50%, 45%, 40%, 35%, 30%, 25%, or 20% of the longitudinal distance from the anterior opening to the posterior opening. The distance between the anterior opening and the button is important because there is a natural distance at which a person will hold the device while cutting. For example, it is awkward to hold the device more than half way from the anterior opening to the posterior opening because the distance reduces the amount of control the user has when manipulating the device during a cutting procedure. Thus, by placing the release button in the area intended to be gripped by the user, the release button is in a location where the user can activate the release button without repositioning the hand following a cutting procedure.

In some embodiments, the release button is actuated by an inward force orthogonal to the longitudinal axis of the housing. Thus, a user can actuate the release button by squeezing in the grip area. The release button may be biased to a non-actuated position thereby requiring a certain amount of force applied by the user to overcome the non-actuated position of the release button.

The release button may positioned on a top side (e.g., top side 94) of the housing. The top side of the housing is the side opposite the cutting edge of the cutting blade. A user will often place a finger on the top side of the housing in order to apply force in the downward direct to cause cutting. By placing the release button on the top side of the housing, the release button will be in a convenient position for actuation by the user. Alternatively, the release button may be placed on a bottom side or lateral side of the housing.

In some embodiments the latch mechanism is automatically activated to a locked position when the slidable insert is moved from the safe position to the activated position. Automatic latching can be important to minimize the number of movements performed by the user. Even when the movement is simple to perform, having too many buttons or mechanisms can make it difficult for a user to figure out which button performs which desired mechanism. In some embodiments, the latch mechanism is activated by a single motion of the user applying pressure to the back button in the longitudinal direction. The automatic latch preferably makes a clicking sound to indicate when the latch has been activated. In order to provide sufficient gripping surface to operate the back button and/or the release button, the housing may be at least 30 mm, 40 mm 50 mm, 60 mm, 70 mm or 80 mm long in the longitudinal direction between the anterior and posterior openings.

With the slidable insert in the exposed position, the back button is positioned posterior to the anterior opening in the longitudinal direction. The distance from the anterior opening to back button in this position can be important for providing sufficient area for gipping the device while activating the blade. In some embodiments, the distance from the anterior opening to the back button (with the slidable insert in the exposed position) is greater than or equal to 20, 25, 30, 35, 40, 45, 50 mm and optionally less than or equal to 100, 80, 60, or 40 mm or within a range of the foregoing points.

The back button may be positioned on a longitudinal post extending from the posterior opening. The longitudinal post may be at least 10, 15, 20, 25, or 30 mm long and/or less than 50, 45, 40, 35, 30, 25, or 20 mm or within a range of the foregoing endpoints.

The back button is preferably protected from accidental activation. Accidental activation may be inhibited or prevented using a protective cover or a lockout mechanism. Examples of lockout mechanisms that can be used include the lockout mechanisms described in U.S. Pat. No. 5,391, 177 to Schwartz, U.S. Pat. No. 5,569,282 to Werner, and U.S. Pat. No. 6,022,364 to Flumene, all of which are hereby incorporated by reference.

The release button may release the latch mechanism upon actuation or may include a second lock that allows the release button to lock the slidable insert in the exposed position until release of the release button.

Posterior Activation Mechanism and Posterior Cover

A second embodiment relates to a scalpel having a back button that activates the blade similar to a ball point pen and has a cover that is coextensive with the back button to inhibit the slidable insert from being accidentally activated.

In some embodiments, the safety cutting device may include an elongate housing having a lengthwise cavity that extends between an anterior opening and a posterior opening. The cavity is configured to receive a slidable insert and allow movement of the slidable insert in a longitudinal direction. A cutting blade is coupled to the slidable insert. The housing forms a sheath configured to cover the cutting blade. The sheath provides the anterior opening through which the blade can be extended. The slidable insert is moveable within the housing between a safe position in which the blade is covered by the sheath and an exposed position in which the blade is extended through the anterior opening and exposed for cutting. A biasing member is operably coupled to the slidable insert and biases the slidable insert to the safe position. The safety cutting device also includes a latch mechanism operable to lock the slidable insert in the exposed position. A back button is formed in or coupled to the slidable insert and extends from the posterior opening in the housing, the back button has a rearward facing engagement surface that upon actuation moves the slidable insert longitudinally from the safe position to the exposed position. A protective cover partially covers the back button. The protective cover extends from the posterior opening toward the engagement surface for a distance sufficient to impede actuation of the back button by a planar surface applying a force in the longitudinal direction.

Unless otherwise specified, for purposes of this invention the planar surface is infinite. Thus, the cover provides a structure that engages the planar surface when contacted perpendicular to the longitudinal direction.

The back button can be angled to provide additional protection against accidental activation of forces that are not perpendicular to the longitudinal direction. The angle of the reward facing surface to the planar surface may be greater than or equal to 5, 10, 15, 20, or 25 degrees and/or less than or equal to 50, 45, 40, 35, 30, or 25 degrees, and/or within a range of the foregoing endpoints. The angle may also be measured according to the longitudinal direction, in which case the foregoing angles are subtracted from 90 degrees.

The back button is preferably positioned on a longitudinal post extending from the posterior opening. The longitudinal post may be greater than or equal to 10, 15, 20, 25, or 30 mm long and/or less than 50, 45, 40, 35, 30, 25, or 20 mm long or within a range of the foregoing endpoints.

The protective cover preferably extends adjacent to the back button and/or the longitudinal post. The distance that the cover needs to extend rearwardly to inhibit a planar surface from exposing the blade will depend on how far the blade is within the cover. The further the blade is retracted within the cover, the more the back button can be pushed forward without causing exposure of the blade. Nevertheless, in some embodiments, the protective cover may extend rearwardly to a position adjacent to or posterior to the back button with the slidable insert in the safe position.

The protective cover may be rigidly fixed to the housing in any manner such as adhesive, ultrasonic welding or a snap connection. However, in a preferred embodiment the protective cover is an extension of the housing material (i.e., an integral part of the housing).

The latch mechanism may be automatically activated to a locked position when the slidable insert reaches the exposed position. The latch mechanism may be activated by a single motion of the user applying pressure to the back button in the longitudinal direction. The latch mechanism may be accomplished using a hook and latch. The cutting device may also include a release button to disengage the hook and latch.

The latch mechanism may be formed from something other than a hook and latch. For example, the latch mechanism may include a guide structure with a w-shaped groove and a protrusion extending from the slidable insert into the w-shaped groove. An example of a pen activation mechanism that uses a slidable insert with a w-shaped groove is disclosed in U.S. Pat. No. 5,571,128 to Shapiro, which is hereby incorporated herein by reference. Another example of a latch mechanism that may be used with this embodiment of the invention is disclosed in U.S. Pat. No. 5,569,282 to Werner, which is incorporated herein by reference.

Anterior Release Mechanism Fixed Longitudinally

Another embodiment relates to a safety cutting device that includes a release button with a flange on the slidable insert or housing. In this embodiment, simple activation and deactivation can be achieved using a minimal number of parts. Minimizing the number of parts may be important for facilitating the manufacture and assembly of the device. A release button that is separate from the housing or slidable insert requires manufacturing and handling a separate part and often requires multiple parts. In a preferred embodiment the release button is biased to the non-actuated position. A release buttons that is not formed with a flange will need a separate biasing member (e.g., spring) to keep the release button in the non-actuated position until user selects the actuated position. Increasing the number of parts can be highly detrimental to the economic viability of the device.

In some embodiments, the safety cutting device may include an elongate housing having a lengthwise cavity that extends between an anterior opening and a posterior opening. The cavity is configured to receive a slidable insert and allow movement of the slidable insert in a longitudinal direction. A cutting blade is coupled to the slidable insert. The housing forms a sheath configured to cover the cutting blade. The sheath provides the anterior opening through which the blade can be extended. The slidable insert is moveable within the housing between a safe position in which the blade is covered by the sheath and an exposed position in which the blade is extended through the anterior opening and exposed for cutting. A biasing member is operably coupled to the slidable insert and biases the slidable insert to the safe position. The safety cutting device also includes a latch mechanism operable to lock the slidable insert in the exposed position. A back button is formed in or coupled to the slidable insert and extends from the posterior opening in the housing, the back button has a rearward facing engagement surface that upon actuation moves the slidable insert longitudinally from the safe position to the exposed position. A release button is formed into the housing or the slidable insert and configured to unlock the latch mechanism upon actuation. The release button is fixed in the axial direction. In one embodiment, the release button may include a flange formed as a single piece with the slidable insert or the housing.

In some embodiments, the functions of actuating the back button, locking the slidable insert in the exposed position, and unlocking the latch mechanism only requires four separate parts, the parts being a single piece slidable insert, a single biasing member such as a spring, and two pieces of housing. In some embodiments, the device can include additional parts for performing different functions. However, preferably, the entire device can be made from the four parts and a cutting blade.

The latch mechanism may be automatically activated to a locked position when the slidable insert reaches the exposed position. The latch mechanism may be activated by a single motion of the user applying pressure to the back button in the longitudinal direction.

The back button may be positioned on a longitudinal post extending from the posterior opening. The longitudinal post may have dimensions as described above.

The release button may be located on the slidable insert and/or may be located on a lateral side of the device. An example of a release button that can be used in this embodiment in combination with a pen activation mechanism is shown in U.S. Pat. No. 6,949,109 to Iske, which is hereby incorporated herein by reference.

Latch Mechanism

In yet another embodiment, the cutting device includes a latch mechanism that locks the slidable insert in the exposed position and the latch is released only upon releasing the release button (i.e., pressing the release button keeps the slidable insert locked and it is only upon release of the release button that the latch is disengaged. Once the latch mechanism is released, the slidable insert is automatically returned to the safe position by the biasing member. In this embodiment, the release button can be pressed down (i.e., initial activation), but the slidable member is not unlocked until the release button is released. This mechanism is advantageous to prevent accidental unlocking of the slidable insert. Preventing accidental unlocking of the slidable insert allows the release button to be made easy to press down or actuate while positioned in a conspicuous location on the housing or slidable insert, which increases the probability of a clinician using the release button and making the device safe.

The cutting device includes an elongate housing having a lengthwise cavity configured to receive the slidable insert. A cutting blade is coupled to the slidable insert. The housing forms a sheath configured to cover the cutting blade and the sheath has an anterior opening through which the blade can be extended. The slidable insert is moveable within the housing in a longitudinal direction between a safe position in which the blade is covered by the sheath and an exposed position in which the blade is extended through the anterior opening and exposed for cutting. A biasing member is operably coupled to the slidable insert and biases the slidable insert to the safe position. A latch mechanism is operable to lock the slidable insert in the exposed position. The latch mechanism is automatically activated to a locked position by movement of the slidable insert from the safe position to the exposed position.

The housing forms a handle that provides a grip for manipulating the cutting device with fingers during cutting. A release button is positioned on the handle and has an actuated position and a non-actuated position. The release button is biased in the non-actuated position. With the release mechanism positioned in the actuated position the release mechanism is configured to unlock the latch mechanism and actuate a second lock mechanism that locks the slidable insert in the exposed position, wherein upon release of the release button by a user, the release button automatically returns to the non-actuated position and unlocks the second lock mechanism, thereby causing the slidable insert to move to the safe position.

In some embodiments the latch mechanism includes a protrusion positioned on a deflectable member of the slidable insert. The protrusion on the deflectable member is configured to engage the housing to lock the slidable insert in the exposed position. To unlock the slidable member, the release button is pressed (i.e., actuated). In the actuated position, the release button deflects the deflectable member to release the lock of the latch.

The second lock mechanism includes a wall on the slidable insert that engages a protrusion on the release button when the release button is in the actuated position, thereby locking the slidable insert in the exposed position.

The cutting device may include a back button formed in or coupled to the slidable insert and extending from a posterior opening in the housing. The back button may have a rearward facing engagement surface that upon actuation moves the slidable insert longitudinally from the safe position to the exposed position.

The invention may also include a method of using a safety scalpel. The method includes providing a cutting device as described herein and then locking the slidable insert in the exposed position using a latch mechanism, actuating a release button, performing a cutting procedure with the release button actuated, and releasing the release button thereby causing the second lock to disengage and enable the bias member to move the cutting blade to the covered position.

In an alternative embodiment, the release activated mechanism described below can be incorporated into a slidable insert or housing of any of the devices disclosed in U.S. Pat. Nos. 5,571,128; 5,569,282; 6,949,109; or similar devices.

Yet another embodiment relates to a cutting device having an automatically locking activation mechanism formed from a latch between slidable insert and the housing. The device may include a biasing member positioned between the housing and the slidable insert. The automatic locking activation mechanism is unlocked using a release button positioned in the anterior portion of the housing.

The cutting device includes an elongate housing having a lengthwise cavity configured to receive the slidable insert. A cutting blade is coupled to the slidable insert. The housing forms a sheath configured to cover the cutting blade and the sheath has an anterior opening through which the blade can be extended. The slidable insert is moveable within the housing in a longitudinal direction between a safe position in which the blade is covered by the sheath and an exposed position in which the blade is extended through the anterior opening and exposed for cutting. A biasing member is operably coupled to the slidable insert and biases the slidable insert to the safe position. A latch mechanism is operable to lock the slidable insert in the exposed position. The latch mechanism is automatically activated to a locked position by movement of the slidable insert from the safe position to the exposed position.

The housing forms a handle. A front portion of the handle provides a grip for manipulating the cutting device with fingers during cutting. A release button is positioned on the anterior portion of the housing and has an actuated position and a non-actuated position. The release button is biased in the non-actuated position. A release button is positioned on the anterior portion of the housing. The release button is configured to unlock the latch mechanism upon actuation, thereby causing the biasing member to return the slidable insert to the safe position.

Any of the foregoing embodiments described above may be used alone or in combination with one another and/or the embodiments disclosed in the references incorporated herein by reference.

The illustrative embodiments described in the detailed description and claims are not meant to be limiting. Other embodiments may be utilized, and other changes may be made, without departing from the spirit or scope of the subject matter presented herein. It will be readily understood that the aspects of the present disclosure, as generally described herein can be arranged, substituted, combined, separated, and designed in a wide variety of different configurations, all of which are explicitly contemplated herein.

We claim:

1. A safety cutting device, comprising: an elongate housing extending between an anterior end and a posterior end thereof and defining a sheath having an anterior opening and forming a cavity configured to receive a slidable insert, the anterior opening having an elongate shape that accommodates a size 10, 11, and/or 15 surgical blade, the housing also defining a handle that extends from an anterior portion of the housing to a posterior portion thereof, the handle providing a grip for a user operating the cutting device; a number 10, 11, or 15 surgical cutting blade coupled to the slidable insert, the slidable insert positioned within the cavity and moveable within the housing between a safe position in which the blade is covered by the sheath and an exposed position in which the blade is extended through the anterior opening and exposed for cutting; a biasing member biasing the slidable insert to the safe position, wherein the housing includes a second cavity and the biasing member is disposed in the second cavity; a latch mechanism operable to lock the slidable insert in the exposed position; and a release mechanism positioned on an anterior portion of the handle and configured to unlock the latch mechanism wherein the anterior portion of the handle is located in a first 50% of a longitudinal distance extending from the anterior opening of the elongate housing to a posterior opening of the elongate housing, and the release mechanism movable in a transverse direction of the housing and fixed in the longitudinal direction of the housing.

2. The cutting device of claim 1, wherein the cutting blade is a number 10 surgical blade.

3. The cutting device of claim 2, wherein the cutting blade is a number 11 surgical blade.

4. The cutting device of claim 1, wherein the housing includes an injection molded part.

5. The cutting device of claim 4, wherein the release mechanism includes an injection molded flange integral with the housing and extending therefrom.

6. The cutting device of claim 1, wherein the release mechanism is positioned on a top side of the housing.

7. The cutting device of claim 1, wherein the latch mechanism automatically locks when the slidable insert reaches the exposed position.

8. The cutting device of claim 1, wherein the housing comprises two injection molded parts that when assembled form the cavity.

9. The cutting device of claim 8, wherein the two injection molded parts that form the housing are joined by ultrasonic welds.

10. The cutting device of claim 1, further comprising a slot formed in the sheath, the slot configured to cut suture passed therethrough when the slidable member is in the safe position.

11. The cutting device of claim 1, wherein the latch mechanism is a hook and latch and the release mechanism includes a protrusion configured to disengage the hook and latch.

12. The cutting device of claim 1, wherein the release mechanism is positioned within 40 mm of an anterior end of the handle.

13. The cutting device of claim 1, wherein the biasing member is a coil spring that is compressed when the slider is in the exposed position.

14. The cutting device of claim 1, wherein the biasing member is a coiled spring.

15. The cutting device of claim 14, wherein the housing includes the posterior opening at a posterior end of the handle, wherein at least a portion of the slider exits the posterior opening and wherein the coil spring extends at least 70% of the distance between the anterior and posterior openings.

16. The cutting device of claim 1, wherein the housing has a trapezoidal cross section.

17. The cutting device of claim 12, wherein the release mechanism is positioned less than 45% of the distance from the anterior opening to a posterior end of the handle portion.

18. The cutting device of claim 1, wherein the release mechanism is positioned less than 45% of the distance from the anterior opening to the posterior end.

19. The cutting device of claim 11, wherein the hook and latch mechanism includes a deflectable member.

20. The cutting device of claim 19, wherein the deflectable member is formed in the slidable insert.

21. A safety cutting device, comprising: an elongate housing extending between an anterior end and a posterior end thereof and defining a sheath having an anterior opening and forming a cavity configured to receive a slidable insert, the anterior opening having an elongate shape that accommodates a size 10, 11, and/or 15 surgical blade, the housing also defining a handle that extends from an anterior portion of the housing to a posterior portion thereof, the handle providing a grip for a user operating the cutting device; a number 10, 11, or 15 surgical cutting blade coupled to the slidable insert, the slidable insert positioned within the cavity and moveable within the housing between a safe position in which the blade is covered by the sheath and an exposed position in which the blade is extended through the anterior opening and exposed for cutting; a biasing member biasing the slidable insert to the safe position; a latch mechanism operable to lock the slidable insert in the exposed position; and a release mechanism positioned on an anterior portion of the handle and configured to unlock the latch mechanism wherein the anterior portion of the handle is located in a first 50% of a longitudinal distance extending from the anterior opening of the elongate housing to a posterior opening of the elongate housing, and the release mechanism movable in a transverse direction of the housing and fixed in the longitudinal direction of the housing, wherein the latch mechanism is a hook and latch and the release mechanism includes an inward projecting protrusion configured to press the hook down in order to disengage the hook from the latch.

* * * * *

UNITED STATES PATENT AND TRADEMARK OFFICE
CERTIFICATE OF CORRECTION

PATENT NO. : 11,179,859 B2
APPLICATION NO. : 14/201658
DATED : November 23, 2021
INVENTOR(S) : Branden D. Rosenhan et al.

Page 1 of 1

It is certified that error appears in the above-identified patent and that said Letters Patent is hereby corrected as shown below:

In the Claims

Claim 19, Column 16, Line 10, the claim number '19' should read -20- and the claim dependency '11' should read -19-.

Claim 20, Column 16, Line 12, the claim number '20' should read -21- and the claim dependency '19' should read -20-.

Claim 21, Column 16, Line 15, the claim number '21' should read -19-.

Signed and Sealed this
Twenty-sixth Day of December, 2023

Katherine Kelly Vidal
*Director of the United States Patent and Trademark Office*